United States Patent
Brown

[11] Patent Number: 5,871,449
[45] Date of Patent: Feb. 16, 1999

[54] DEVICE AND METHOD FOR LOCATING INFLAMED PLAQUE IN AN ARTERY

[76] Inventor: David Lloyd Brown, 7103 Monte Vista Ave., La Jolla, Calif. 92037

[21] Appl. No.: 774,022

[22] Filed: Dec. 27, 1996

[51] Int. Cl.[6] ........................................................ A61B 6/00
[52] U.S. Cl. ............................................ 600/474; 600/549
[58] Field of Search ..................................... 600/473, 474, 600/549, 407, 479

[56] References Cited

U.S. PATENT DOCUMENTS

| | | |
|---|---|---|
| Re. 32,204 | 7/1986 | Halvorsen . |
| 3,273,395 | 9/1966 | Schwarz . |
| 3,913,568 | 10/1975 | Carpenter . |
| 4,005,605 | 2/1977 | Michael . |
| 4,602,642 | 7/1986 | O'Hara et al. . |
| 4,699,147 | 10/1987 | Chilson et al. . |
| 4,777,955 | 10/1988 | Brayton et al. . |
| 4,784,149 | 11/1988 | Berman et al. ........................ 600/474 |
| 4,790,324 | 12/1988 | O'Hara et al. . |
| 4,797,840 | 1/1989 | Fraden . |
| 4,862,887 | 9/1989 | Weber et al. . |
| 5,237,996 | 8/1993 | Waldman et al. . |
| 5,623,940 | 4/1997 | Daikuzono ............................ 600/439 |
| 5,733,739 | 3/1998 | Zakin et al. ............................ 435/29 |

FOREIGN PATENT DOCUMENTS

WO 97/10748  3/1997  WIPO .

OTHER PUBLICATIONS

Buja et al., *Role of Inflammation in Coronary Plaque Disruption*, pp. 503–505, Circulation, vol. 89, No. 1, Jan. 1994.

van der Wal et al., *Site of Intimal Rupture or Erosion of Thrombosed Coronary Atherosclerotic Plaques Is Characterized by an Inflammatory Process Irrespective of the Dominat Plaque Morphology*, pp. 36–44, Circulation, vol. 89, No. 1, Jan. 1994.

Muller et al., *Triggers, Acute Risk Factors and Vulnerable Plaques: The Lexicon of a New Frontier*, pp. 809–813, JACC, vol. 23, No. 3, Mar. 1, 1994.

Falk et al., *Coronary Plaque Disruption*, pp. 657–671, Circulation, vol. 92, No. 3, Aug. 1, 1995.

Casscells et al., *Thermal detection of cellular infiltrates in living atherosclerotic plaques: possible implications for plaque rupture and thrombosis*, pp. 1447–1449 and 1422, The Lancet, vol. 347, May 25, 1996.

*Primary Examiner*—Brian Casler
*Attorney, Agent, or Firm*—Nydegger & Associates

[57] ABSTRACT

A system for locating inflamed plaque in an artery of a patient includes a catheter with an expander mounted at a catheter distal end. An infrared carrier, e.g., an optical fiber is mounted on the catheter with a carrier distal end attached to the expander. A sensor is connected to a carrier proximal end to measure infrared radiation transmitted through the carrier from the carrier distal end. In use, the expander is operable to selectively move the carrier distal end into contact with the arterial wall. Infrared radiation can then be measured to determine the temperature at the arterial wall. Temperatures at various locations can be taken, with elevated temperatures being indicative of inflamed plaque.

22 Claims, 2 Drawing Sheets

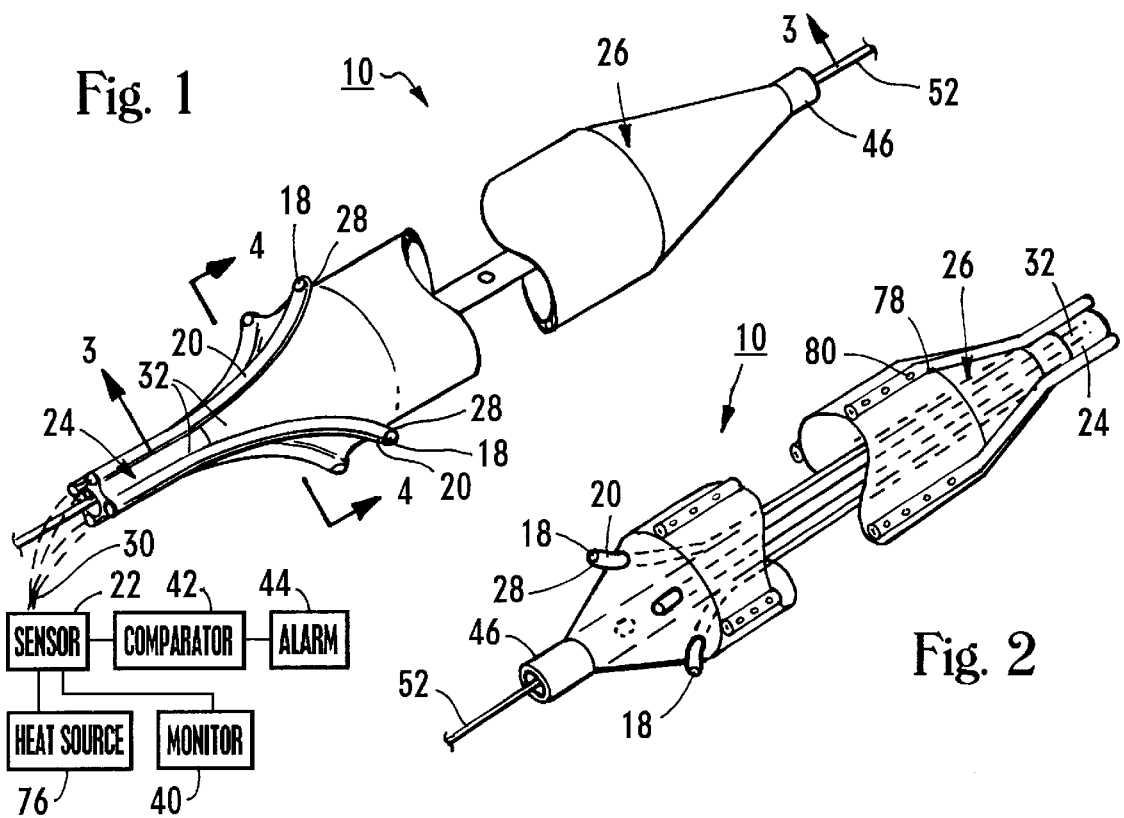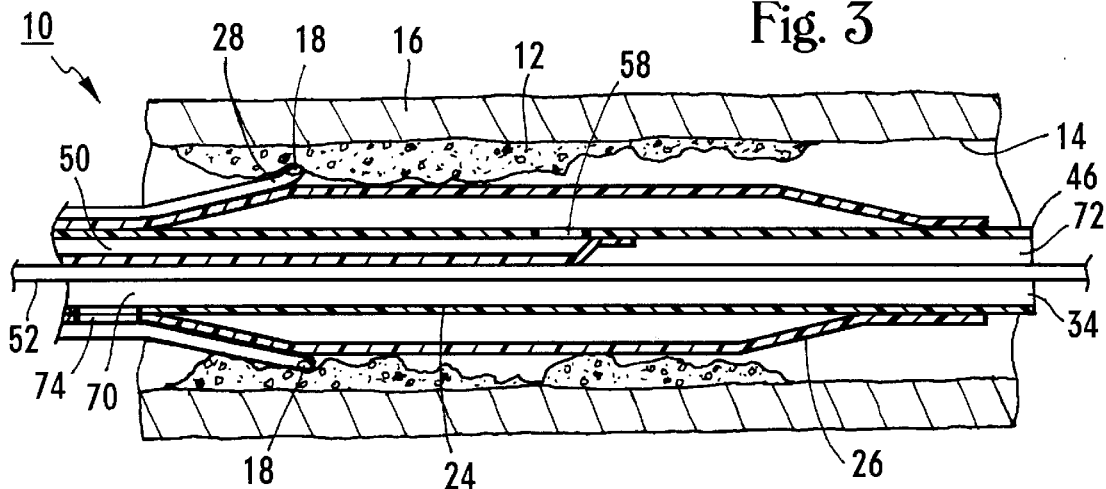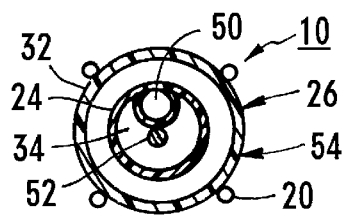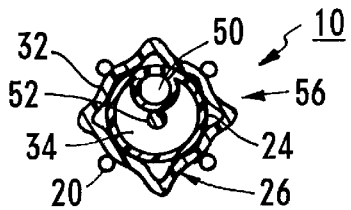

DEVICE AND METHOD FOR LOCATING INFLAMED PLAQUE IN AN ARTERY

FIELD OF THE INVENTION

The present invention pertains generally to medical devices and methods for locating plaque in an artery. The present invention is particularly useful for locating inflamed or unstable plaque in an artery.

BACKGROUND

Plaque can develop in different locations in a patient's cardiovascular system. The plaque can vary in size and shape. For example, the plaque can be quite extensive and occlude a substantial length of the vessel. Alternately, the plaque can be quite short and small.

Further, the condition of the plaque can vary. For example, the plaque can be inflamed and unstable, or the plaque can be quite stable. It is important to recognize that, inflamed and unstable plaque is subject to rupture, erosion or ulceration which can cause the patient to experience a myocardial infarction.

Presently, a number of procedures are available for locating plaque in an artery. One commonly performed procedure is angiography, which involves taking x-ray pictures of vessels after injecting a radiopaque substance into the vessels. While this procedure is quite effective for locating large plaque in arteries, this procedure is unable to evaluate whether the plaque is inflamed and unstable. Therefore, there is a need of a device and procedure for precisely and accurately locating the position of unstable, inflamed plaque.

In light of the above, it is an object of the present invention to provide a device and method for locating unstable, inflamed plaque in an artery. Another object of the present invention is to provide a system for determining the size of the unstable, inflamed plaque in the artery. Another object of the present invention is to provide a device and method for locating inflamed plaque which is relatively easy and inexpensive to manufacture and relatively easy to operate.

SUMMARY

The present invention is directed to a device and method which satisfies the objectives for locating inflamed plaque on the wall of an artery of a patient. A device having features of the present invention, includes at least one detector for receiving information about the artery wall, a sensor for determining the presence of inflamed plaque based upon the information received from the detector, a carrier for transferring information from each detector to the sensor, and an expander for selectively positioning each detector proximate the artery wall.

Importantly, unstable and inflamed plaque can cause the temperature of the artery wall to elevate up to two and a half degrees Centigrade or Celsius proximate the inflamed plaque. With the present invention, each detector is inserted into the artery to receive infrared radiation from the artery wall. The infrared radiation is subsequently transferred with the carrier to the sensor. The sensor determines temperature at each detector based upon the infrared radiation received from each detector. Therefore, the present invention is able to locate inflamed plaque by monitoring the artery wall for elevated temperatures.

Typically, each detector includes a single carrier for transferring the infrared radiation to the sensor. As provided herein, each carrier can be an optical fiber and each detector can be an aperture formed on the optical fiber which contacts the artery wall. Preferably, a plurality of detectors are positioned circumferentially around the expander to decrease the chance of the detectors missing small inflamed plaque.

Optimally, the device includes a radiopaque marker which is positioned proximate each detector so that the location of the detector in the artery can be determined with a fluoroscope.

The sensor can include a monitor, a comparator and an alarm. The monitor displays and/or records temperature at each detector as the detectors are moved through the artery. The comparator determines whether a temperature difference exists between each detector and whether a temperature change occurs at each detector. The alarm indicates when the temperature difference or the temperature change exceeds a predetermined value. Since inflamed plaque can cause the temperature of the artery wall to elevate up to two and a half degrees Centigrade or Celsius, the predetermined value is typically between 0.5–2.5 degrees Centigrade or Celsius. When the predetermined value is exceeded, the inflamed plaque is located.

The expander is moveable between a first configuration and a second configuration. Typically, the first configuration is dimensioned for insertion of the detectors into the artery and the second configuration is dimensioned for positioning the detectors proximate to the artery wall. An inflatable balloon makes an excellent expander. Additionally, the expander can be used to simultaneously dilate the artery.

Preferably, the device also includes at least one flow passageway which allows for the flow of blood past the expander when the expander is substantially in its second configuration. Thus, the flow passageway allows the present device to be used in an artery without interrupting blood flow in that artery.

The invention is also a method for locating inflamed plaque in an artery of a patient. The method comprises the steps of inserting the expander into the artery of the patient, selectively operating the expander to selectively position the detector at the artery wall of the patient, and determining the temperature of the artery wall at each detector with the sensor.

It is important to recognize that a device, in accordance with the present invention can accurately locate inflamed plaque by locating elevated temperatures of the artery wall. Thus, the inflamed plaque may be treated prior to the life threatening rupture or ulceration.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a device having features of the present invention;

FIG. 2 is a perspective view of a second embodiment of a device having features of the present invention;

FIG. 3 is a side cut-away view taken on line 3—3 and positioned in an artery;

FIG. 4A is a side cut-away view taken on line 4—4 of FIG. 1 with an expander in a first configuration;

FIG. 4B is a cut-away view taken of line 4—4 of FIG. 1 with the expander in a second configuration;

DESCRIPTION

Figure 5A:
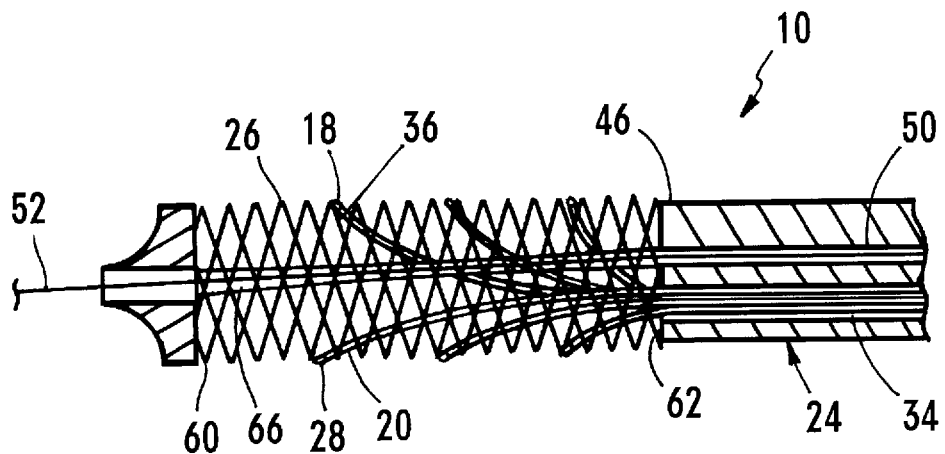
FIG. 5A is a side cut-away view of a third embodiment of a device having features of the present invention with an expander in a first configuration.

The present invention is a device 10 and method which are particularly suited for locating unstable, inflamed plaque 12 on an artery wall 14 of an artery 16. Referring initially to FIG. 1, the device 10 includes at least one detector 18, at least one carrier 20, a sensor 22, a catheter 24, and an expander 26. The temperature of the inflamed plaque 12 is elevated approximately 0.5 to 2.5 degrees Centigrade or Celsius. The present device 10 locates the unstable, inflamed plaque 12 by measuring the temperature of the artery wall 14 as the device is moved through artery 16 and locating areas of elevated temperature.

In the embodiment shown in the Figures, each detector 18 receives infrared radiation from the artery wall 14 and each detector 18 is an aperture proximate a carrier distal end 28 of each carrier 20 which exposes the carrier 20 to the artery wall 14. Alternately, for example, each detector 18 can be projection (not shown) which extends between the artery wall 14 and the carrier 20.

Figure 5B:
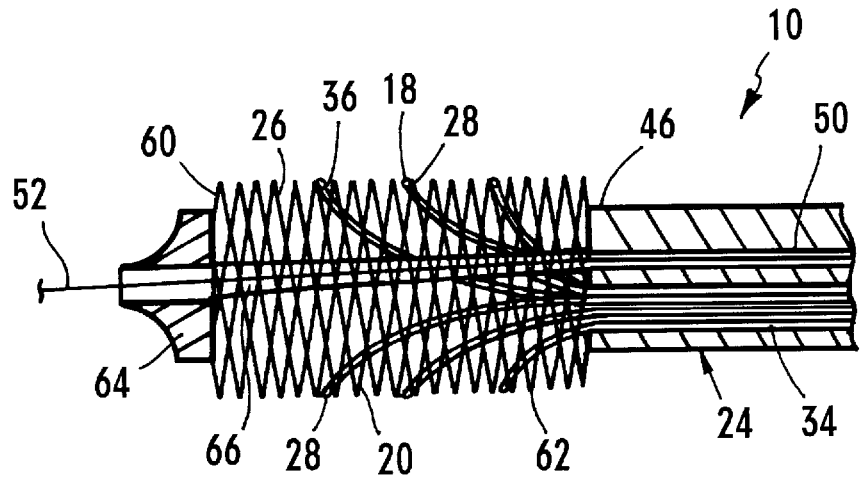
FIG. 5B is a side cut-away view of the embodiment of FIG. 5A with the expander in a second confirmation.

Preferably, the device 10 includes a plurality of detectors 18 positioned circumferentially around the expander 26 so that the temperature can be monitored around the circumference of the artery wall 14. The sensitivity of the device 10 increases as the number of detectors 18 increases, since small inflamed plaque 12 is less likely to pass between the detectors 18. In the embodiments shown in the FIGS. 1–4, the device includes four, circumferentially, spaced apart detectors 18. Importantly, the positioning of the detectors 18 on the expander 26 can vary. For example, as shown in FIGS. 5A and 5B the device 10 can include a plurality of detectors 18 spaced apart axially along the expander 26 for additional sensitivity. Also, the detectors 18 can be staggered along the expander 26.

The carrier 20 transmits the infrared radiation from each detector 18 to the sensor 22. In the embodiments shown in the Figures, each detector 18 includes a separate carrier 20 for transferring the infrared radiation to the sensor 22. As provided herein each carrier 20 can an optical fiber having an aperture at the carrier distal end 28 which forms each detector 18. As shown in phantom in FIG. 1, a carrier proximal end 30 of each carrier 20 is attached to the sensor 20. Any optical fiber which transmits infrared radiation should make a suitable carrier 20.

The carrier 20 can be secured to the catheter 24 and expander 26 in a number of alternate ways. For example, in the embodiment shown in FIGS. 1, 3, 4A and 4B, the carriers 20 are positioned and secured to an outer surface 32 of the catheter 20 and expander 26. Alternately, in the embodiment shown in FIG. 2, the carrier 18 can extend through apertures in the expander 26. In yet another embodiment shown in FIGS. 5A and 5B, the carrier 20 can extend through a first lumen 32 of the catheter 24 and through the expander 26.

Preferably, the device 10 includes a marker 36 positioned proximate each detector 18 so that the location of each detector 18 can be determined. For example, each marker 36 can be a radiopaque material, such as silver which is deposited on each carrier 20 proximate each detector 18. In this version, the position of the radiopaque marker 36 is visible with x-rays and a fluoroscope.

The sensor 22 receives the information, i.e., the infrared radiation from each detector 18 through each carrier 20 and determines temperature at each detector 18 based upon the infrared radiation received or determines if a change of temperature occurs at each detector 18. Preferably, the sensor 22 receives infrared radiation from a plurality of detectors 18 and determines the temperature or a temperature difference at each detector 18. The sensor 22 may be any suitable infrared radiation sensor. For example, a sensor 22 made with a suitable pyroelectrical material can be utilized. As is well known to those skilled in the art, pyroelectric material generates an electric charge that is related to the amount of temperature change in the pyroelectric material.

The sensor 22 can include a monitor 40, a comparator 42 and an alarm 44. The monitor 40 displays and/or records the temperature at each detector 18 for review as the device 10 is moved in the artery 16. The comparator 42 compares the temperature between the detectors 18 to determine whether a temperature difference exists between the detectors 18. Further, the comparator 42 also compares the temperature at each detector 18 to determine whether a temperature change occurs at each detector 18 as the device is moved in the artery.

The alarm 44 is connected to the comparator 42 and notifies the user of the device 10, i.e., a surgeon, when the temperature difference between each detector 18 or the temperature change exceeds a predetermined value. For example, if the temperature difference or the temperature change is above the predetermined value, e.g., approximately 0.5–2.5 degrees Centigrade or Celsius, the alarm 44 will notify the user. The alarm 44 can be implemented in a number of alternate ways, such as, an audio signal, i.e., a bell, or a visual signal, i.e., a digital readout.

The catheter 24 is used to position the expander 26 and the detectors 18 in the proper location in the artery 16. Typically, the catheter 24 is cylindrical or elongated shaped and has a catheter distal end 46 which is inserted into the artery 16 and a catheter proximal end (not shown) which is outside the artery 16 for manipulating the catheter 24 in the artery 16. Preferably, the catheter 24 is formed from a flexible and somewhat stiff material such as PET to facilitate movement through the artery 10.

The design of the catheter 24 varies according to the design of the expander 26. For example, the catheter 24 can include the first lumen 34 (as discussed previously) and a second lumen 50. Referring to FIG. 3, the first lumen 34 can carry a guidewire 52 for guiding the catheter 24 in the artery 16 or as shown in FIGS. 5A and 5B can retain the carriers 20. As discussed below, the second lumen 50 can facilitate movement of the expander 26 between a first configuration 54 (shown in FIG. 4A) and a second configuration 56 (as shown in FIG. 4B).

The expander 26 selectively positions the detectors 18 proximate the artery wall 14. Further, the expander 26 provided herein can also be used to dilate the artery 16.

The expander 26 at least moves between the first configuration 54 for insertion into the artery 16 and the second configuration 56. As shown in FIGS. 1–4, the expander 26 can be an inflatable balloon attached proximate to the catheter distal end 28. Referring now to FIG. 3, fluid (not shown) may pass from a pressurized fluid source (not shown) through the second lumen 50 and a balloon aperture 58 in the second lumen 50 to selectively inflate the expander 26. Inflation of this nature may be appreciated by comparison of FIG. 4A, where the balloon is shown in the first configuration 54, and FIG. 4B, where the balloon is shown substantially in the second configuration 56. For the purposes of the present invention, numerous devices, e.g., pumps or syringes may be adapted to function as a source of fluid pressure.

It may be seen in FIG. 3, that when the expander 26 moves towards its second configuration 56, each detector 18 contacts the artery wall 14. It may be appreciated that the expander 26 may be expanded more or less than the expansion shown in FIG. 3.

Alternate embodiments of the expander 26 are also possible. For example, as shown in FIGS. 5A and 5B, the expander 26 can be a cylindrical sleeve that is attached to the catheter distal end 46. The cylindrical sleeve is preferably formed from a wire mesh and has a sleeve distal end 60 and a sleeve proximal end 62. The sleeve proximal end 62 is attached to the catheter distal end 46. A grommet 64 is attached to the sleeve distal end 60.

Continuing with FIGS. 5A and 5B, it may be seen that an actuator wire 66 can pass through the second lumen 50 and connect to the grommet 64. In this embodiment, the positioning guidewire 52 extends through a positioning guidewire lumen in the actuator wire 66.

The actuator wire 66 is movable within the second lumen 50 to cause the grommet 64 to move translationally. Translational movement of the grommet 64 moves the sleeve distal end 60 translationally towards, or translationally away from, the catheter distal end 46. Movement of this type may be visualized by comparison of FIG. 5A and FIG. 5B. In particular, it may be seen in FIG. 5A that cylindrical sleeve has a shorter overall length than cylindrical sleeve shown in FIG. 5B. Comparison of FIGS. 5A and 5B also shows that the decrease in overall length of the cylindrical sleeve is accompanied by a corresponding increase in the overall width of the cylindrical sleeve. In this fashion, the actuator wire 66 may be manipulated to selectively expand the cylindrical sleeve.

Preferably, the present device 10 also includes at least one flow passageway 70 which allows for the flow of fluids, e.g., blood past the expander 26 when the expander 26 is proximate the second configuration 56. Referring to FIG. 3, the flow passageway 70 can include a first port 72 and a second port 74 which are in fluid communication with the first lumen 34 and the artery 16 on each side of the expander 26.

Alternately, in the embodiment shown in FIGS. 5A and 5B, a series of apertures (not shown) can be formed in the grommet 64 which allows for the passage of fluid, e.g., blood past the expander 26. In yet another embodiment, the expander 26 can be ribbed (not shown) or include grooves (not shown) which form the flow passageway 70 and allow for the flow of blood past the expander 26.

Preferably, the device also includes a heat source 76 which can be connected to the carriers 20 for heating the inflamed plaque 12. In certain situations, it is desirable to treat inflamed plaque 12 with heat. Therefore, the present invention allows the inflamed plaque 12 to be treated almost immediately. The amount of heat which can be applied to the plaque 12 can vary. It is anticipated that a heat source 76 which supplies sufficient heat through the carriers 20 to heat the artery wall 14 to about 40–45 degrees centigrade is desirable.

Additionally, referring to FIG. 2, the expander 26 can also include one or more fluid passageways 78 having opening 80 for delivering fluid medications to the inflamed plaque 12. This allows expander 26, for example to immediately apply medications to the inflamed plaque 12 which can seal the inflamed plaque 12, thereby inhibiting erosion or rupture. An inflatable balloon having delivery conduits is disclosed in U.S. Pat. No. 5,336,178, Kaplan et al. which is incorporated herein by reference.

Further, it is anticipated that the expander 26, in some instances, can be expanded to preform angioplasty or deliver a supporting stent (not shown).

OPERATION

The operation of the present invention, is best appreciated with reference to FIGS. 1 and 3, and begins with insertion of the guidewire 52 into the artery 16. Next, the device 10 is inserted into the artery 16 over the guidewire 52, with the expander 26 in substantially its first configuration 54. The advancement of the device 10 will continue until the expander 26 is at the position where testing of the artery 16 is to begin.

Next, the expander 26 is moved from its first configuration 54 toward its second configuration 56. If the expander 26 is a balloon, fluid is supplied under pressure through the second lumen 50 to inflate the balloon. The expansion of the expander 26 functions to move the detectors 18 to contact the artery wall 14.

Once the detectors 18 are against the artery wall 14, the plurality of detectors 18 begin receiving infrared radiation from the artery wall 14 which is transmitted through the carriers 20 to the sensor 22. The sensor 22 receives the infrared radiation and determines the temperature at each detector 18. The monitor 40 displays and/or records the temperature at each detector 18. The comparator 42 compares the temperature at the detectors 18 to determine if a temperature difference exists between the detectors 18. If the temperature difference exceeds the predetermined value, the alarm notifies the user of the device 10 and the inflamed plaque 12 is located.

Next, the expander 26 is moved in the artery 16 with the detectors 18 proximate the artery wall 14. Alternatively, the expander 26 may be returned to its first configuration 54 for movement to a different site and then returned to proximate its second configuration 56, with the detectors 18 proximate the artery wall 14.

As the detectors 18 are moved in the artery 16, the sensor 22 continues to determine the temperature at each detector 18 and the comparator 42 continues to determine whether a temperature difference exists between the detectors 18. Further, during this time, the comparator 42 compares the temperatures to determine if a temperature change occurs at any of the detectors 18. Again, if the temperature difference or the temperature change exceeds the predetermined value, the alarm 44 notifies the user of the device 10.

It is important to recognize that the expander 26 can be moved between its first and second configurations 54, 56 as necessary to facilitate movement of the device 10 through the artery 16 and to keep the detectors 18 proximate the artery wall 14.

It is also important to recognize that the size of the inflamed plaque 12 can also be determined from the temperatures as the device 10 is moved through the artery 16.

Further, it is anticipated that the present device 10 can be used in conjunction with existing procedures such as angiography to precisely locate inflamed plaque 12.

While the particular device as herein shown and disclosed in detail is fully capable of obtaining the objects and providing the advantages herein before stated, it is to be understood that it is merely illustrative of the presently preferred embodiments of the invention. For example, it is envisioned that an ultrasound device (not shown) can be attached to the expander 26 and may be utilized to determine the condition of the plaque. Therefore, no limitations are intended to the details of construction or design herein shown other than as described in the appended claims.

What is claimed is:

1. A device for locating inflamed plaque on an artery wall of an artery of a patient, the device comprising:

a plurality of detectors, each detector being insertable into the artery, and being adapted for receiving information about the artery wall of the patient;

a sensor for receiving the information from the detectors and determining the presence of inflamed plaque based upon the information received from the detectors; and an expander for selectively positioning each detector proximate the artery wall in the artery; wherein the detectors are spaced apart substantially around a circumference of the expander.

2. The device of claim 1 wherein each detector receives infrared radiation from the artery wall.

3. The device of claim 1 further comprising a plurality of carriers, each carrier being at least party insertable into the artery for transferring information from each detector to the sensor; wherein each carrier is an optical fiber and each detector is formed as an aperture on each optical fiber.

4. The device of claim 1 wherein the sensor comprises:

a monitor for monitoring temperature at each detector based upon the information received from each detector;

a comparator for determining a temperature difference between each detector; and an alarm for indicating when said temperature difference exceeds a predetermined value.

5. The device of claim 1 wherein the sensor comprises:
a monitor for monitoring temperature at each detector;
a comparator for determining whether a temperature change occurs at each detector;
an alarm for indicating when the temperature change exceeds a predetermined value.

6. The device of claim 1 wherein the expander selectively moves between a first configuration and a second configuration and the device includes at least one flow passageway which allows for the flow of blood past the expander when the expander is proximate its second configuration.

7. The device of claim 1 further comprising a catheter having a catheter distal end and the expander is attached proximally adjacent to the catheter distal end.

8. The device of claim 7 wherein the catheter is formed with a first lumen and a second lumen, wherein the expander is an inflatable balloon and the first lumen includes a first port proximate the catheter distal end and a second port located proximal to said balloon to establish a flow passageway through the first lumen between the first and second ports for the perfusion of blood therethrough when the balloon is inflated.

9. The device of claim 1 wherein the expander comprises:

a mechanism moveable between a first configuration and a second configuration, the first configuration being dimensioned for insertion of into the artery and the second configuration being dimensioned for positioning the detector proximate in the artery wall; and an actuator engaged with the mechanism for moving the mechanism between the first configuration and the second configuration.

10. A device for locating inflamed plaque on an artery wall of an artery of a patient, the device comprising:

a plurality of detectors, insertable into the artery, for receiving information from the artery wall;

a sensor for receiving information from each detector and determining temperature at each detector based upon the information received, the sensor including a comparator for determining a temperature difference between each of the detectors and determining a temperature change at each detector; and an expander movable between a first configuration and a second configuration for selectively positioning the detectors against the artery wall; wherein the detectors are spaced apart substantially around a circumference of the expander.

11. The device of claim 10 wherein the sensor includes an alarm for indicating when the temperature difference exceeds a predetermined value.

12. The device of claim 10 wherein the sensor includes an alarm for indicating when the temperature change exceeds a predetermined value.

13. The device of claim 10 wherein the expander selectively moves between a first configuration and a second configuration and the device includes at least one flow passageway which allows for the flow of blood past the expander when the expander is proximate its second configuration.

14. A method for determining a temperature at an artery wall of an artery, the method comprising the steps of:

advancing an expander in the artery while the expander is at a first configuration;

moving the expander to proximate a second configuration so that a plurality of detectors, which move with the expander substantially contact the artery wall so that each detector can receive information about the artery wall, the detectors being spaced apart substantially around a circumference of the expander;

transmitting the information from each detector to a sensor; and determining the temperature of the artery wall at each detector with the sensor.

15. The method of claim 14 comprising the step of monitoring the temperature at each detector.

16. The method of claim 14 comprising the step of comparing the temperature at each detector to determine whether a temperature change occurs at each detector and to determine whether a temperature difference occurs between each detector.

17. The method of claim 16 comprising the step of indicating when one of the temperature change and the temperature difference exceeds a predetermined value.

18. The method of claim 14 comprising the step of transmitting heat from a heat source through at least one carrier to the artery wall.

19. The method of claim 14 comprising the step of releasing a fluid from a fluid passageway to the artery wall.

20. A device for locating inflamed plaque on an artery wall of an artery of a patient, the device comprising:

at least one detector, insertable into the artery, and being adapted for receiving information about the artery wall of the patient;

a sensor for receiving the information from the detector and determining the presence of inflamed plaque based upon the information received from the detector;

an expander for selectively positioning each detector proximate the artery wall in the artery, the expander being adapted to selectively move between a first configuration and a second configuration; and at least one flow passageway which allows for the flow of blood past the expander when the expander is proximate its second configuration.

21. The device of claim 20 including a plurality of detectors which are spaced apart substantially circumferentially around the expander.

22. A method for locating inflamed plaque on an artery wall of an artery of a patient, the method comprising the steps of;

advancing an expander in the artery while the expander is at a first configuration;

moving the expander to a second configuration so that a detector, which moves with the expander, contacts the artery wall, the detector being adapted to receive information about the artery wall;

transferring the information from the detector to a sensor; and determining the presence of inflamed plaque based upon the information received from the detector.

* * * * *

UNITED STATES PATENT AND TRADEMARK OFFICE
CERTIFICATE OF CORRECTION

PATENT NO.    : 5,871,449
DATED         : February 16, 1999
INVENTOR(S)   : David Lloyd Brown It is certified that error appears in the above-identified patent and that said Letters Patent is hereby corrected as shown below:

Drawings,
The figure indicated as "Fig. 4A" should instead be labeled as "Fig. 4B". The figure indicated as Fig. 4B" should instead be labeled as "Fig. 4A".

Signed and Sealed this

Fifth Day of August, 2003

JAMES E. ROGAN
*Director of the United States Patent and Trademark Office*